United States Patent [19]

Toner et al.

[11] Patent Number: 4,795,712

[45] Date of Patent: Jan. 3, 1989

[54] CALCIUM COMPLEXING DYES AND THEIR USE IN ANALYTICAL COMPOSITIONS, ELEMENTS AND METHODS

[75] Inventors: John L. Toner, Webster; Bruce J. Murray, Walworth; Bruce E. Babb, Rochester; Michael W. Sundberg, Penfield, all of N.Y.

[73] Assignee: Eastman Kodak Company, Rochester, N.Y.

[21] Appl. No.: 37,303

[22] Filed: Apr. 10, 1987

[51] Int. Cl.[4] ............................................. G01N 31/22
[52] U.S. Cl. ............................. 436/74; 260/396 N; 422/56; 422/57; 422/58; 436/79; 436/169; 534/788; 534/795; 534/860; 534/871; 540/1; 548/436; 548/182; 548/190; 549/13
[58] Field of Search ............... 534/788, 795, 860, 876; 540/1; 548/436, 182, 190; 549/13; 260/396 N; 422/56, 57, 58; 436/79, 169, 74

[56] References Cited

U.S. PATENT DOCUMENTS

| | | |
|---|---|---|
| 3,121,613 | 2/1964 | Bittner . |
| 3,754,865 | 8/1973 | Gindler ........................ 436/19 |
| 3,798,000 | 3/1974 | Helger ........................ 436/79 |
| 3,992,158 | 11/1976 | Przybylowicz et al. ........... 422/57 |
| 4,258,001 | 3/1981 | Pierce et al. .................. 422/56 |
| 4,303,610 | 12/1981 | Sardisco et al. ............... 422/61 |
| 4,382,122 | 5/1983 | Mezei et al. .................. 436/74 |
| 4,594,225 | 6/1986 | Argi et al. ................... 422/56 |
| 4,603,209 | 7/1986 | Tsien et al. .................. 548/236 |

OTHER PUBLICATIONS

Tsien, *Biochem.*, 19, pp. 2396–2404 (1980).

*Primary Examiner*—Barry S. Richman
*Assistant Examiner*—Jill Johnston
*Attorney, Agent, or Firm*—J. Lanny Tucker

[57] ABSTRACT

Novel chromogenic derivatives of 1,2-bis-(o-aminoaryloxy)ethane-N,N,N',N'-tetraacetic acid are useful for the determination of calcium ions in both solution and dry assays. These compounds comprise a dye moiety which is directly conjugated to the acetic acid substituted-nitrogen atom and which enables the compounds to exhibit maximum absorbance at a wavelength generally greater than 400 nm before complexation. When the compounds are complexed with calcium ions, the absorbance shifts to a shorter wavelength.

16 Claims, No Drawings

CALCIUM COMPLEXING DYES AND THEIR USE IN ANALYTICAL COMPOSITIONS, ELEMENTS AND METHODS

FIELD OF THE INVENTION

The present invention relates to clinical chemistry. In particular, it relates to novel calcium ion complexing agents and to analytical compositions, elements and methods using same.

BACKGROUND OF THE INVENTION

The determination of the calcium content of various aqueous liquids is important for many manufacturing and environmental purposes. For example, it is often necessary to know the amount of calcium in wastewater, groundwater, food products, chemical processing fluids, oil well water or other natural or effluent liquid sources.

It is also important for diagnostic purposes to determine the calcium content in biological fluids. The calcium level is normally relatively constant in most body fluids. Change in calcium concentration in blood serum can indicate several pathological conditions. For example, hypercalcemia occurs in the hyperfunction of the parathyroid glands and the thyroid glands, in sarcoidosis and in several metastasizing carcinomas. Hypercalcemia is also connected with osteoporosis and osteoplastic carcinomas, acute pancreatitis and acidosis.

A number of chemical and physical procedures are known for the determination of calcium. Direct colorimetric procedures are preferred over tedious precipitation, gravimetric or titrimetric procedures. Generally, such colorimetric procedures involve the complexation of a dye with calcium ions to provide a measurable shift in dye absorption. Several colorimetric assays are described in U.S. Pat. Nos. 3,754,865 (issued Aug. 28, 1973 to Gindler) and 3,798,000 (issued Mar. 19, 1974 to Helger).

A potential problem in the determination of calcium ions in most fluids is the presence of potentially interfering ions (for example, magnesium or phosphates) or large molecules (for example, proteins or bilirubin). Magnesium ions present a particularly difficult problem because they tend to complex to the same compounds that complex with calcium ions. According to the art noted above, magnesium ions can be removed physically from the test sample prior to calcium determination or masked with a magnesium-specific complexing reagent.

A relatively recent advance in clinical chemistry was the development of thin-film multilayer analytical elements such as those described in U.S. Pat. Nos. 3,992,158 (issued Nov. 16, 1976 to Przybylowicz et al) and 4,258,001 (issued Mar. 24, 1981 to Pierce et al). These elements generally have a porous spreading layer and a reagent layer on a nonporous support. One such element has been designed for the determination of calcium ions and is marketed as a KODAK EKTACHEM Clinical Chemistry Slide by Eastman Kodak Co. (Rochester N.Y.). This element contains an arsenazo dye which selectively complexes with calcium ions to provide a detectable dye shift. However, environmental concerns regarding arsenic have prompted workers in the art to find new calcium complexing compounds.

Highly selective compounds for calcium ions are described by Tsien in *Biochem.*, 19, pp. 2396–2404 (1980). The parent compound described therein is 1,2-bis(o-aminophenoxy)ethane-N,N,N',N'-tetraacetic acid, commonly known as BAPTA. These compounds suffer from the disadvantage, however, that they absorb in the ultraviolet region of the electromagnetic spectrum. However, other species, such as bilirubin, hemoglobin and other porphorin species, and metabolic by-products of porphorins, found in analyte solutions such as blood plasma, spinal fluid, urine and other body fluids, also absorb in the UV and short visible wavelength portions of the electromagnetic spectrum, and produce background interference with standard colorimetric equipment and procedures. Therefore, it would be desirable to have highly selective calcium complexing compounds which would be detectable at longer wavelengths, and which would shift to other wavelengths when complexed with calcium to allow quantitative analysis for calcium without interference from UV and short wavelength visible light-absorbing species.

SUMMARY OF THE INVENTION

The problems noted above are ovecome with the use of a substituted or unsubstituted compound of the structure

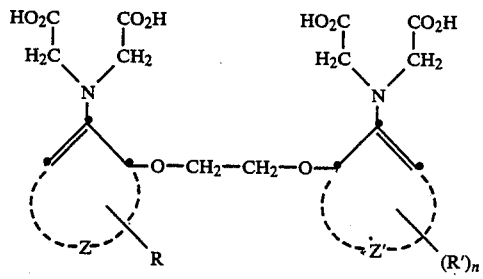

wherein Z and Z' independently represent the carbon and hetero atoms necessary to complete a 5- to 10-membered substituted or unsubstituted aromatic, unsaturated carbocyclic or unsaturated heterocylic ring, R is a dye moiety which is directly conjugated through the aromatic, carbocyclic or heterocyclic ring to the nitrogen atom, each R' is independently formyl, substituted or unsubstituted alkyl, substituted or unsubstituted acyl or halo, and n is 0, 1 or 2, the compound exhibiting a maximum absorption greater than about 400 nm in the absence of calcium ions.

This invention also provides an aqueous composition buffered to a pH of from about 6 to about 9 and containing the compound described above.

An analytical element for the determination of calcium ions comprises an absorbent carrier material containing the compound described above.

Further, a method for the determination of calcium ions comprises the steps of:

A. contacting a sample of a liquid suspected of containing calcium ions with the compound described above, and B. determining the optical density change resulting from the complexation of calcium ions with the compound.

Use of the compounds of this invention provides a highly sensitive means for determination of calcium ions in either a solution or dry assay. An optical density change occurs when they complex with calcium ions. Generally, this change results from a shift in absorbance maximum to a shorter wavelength. In addition, the compounds are highly selective for calcium ions over magnesium ions and provide a highly sensitive means for measuring calcium ions in a wide variety of fluids. The compounds of this invention provide improved sensitivity for calcium ions over BAPTA which is described above. This improved sensitivity is achieved because one of the conjugated rings of the novel compounds of this invention is substituted with a dye moiety.

DETAILED DESCRIPTION OF THE INVENTION

The present invention relates to the determination (qualitative or quantitative measurement) of calcium ions in aqueous liquids. In particular, the invention can be used to assay oil well water, waste-water, cooling water, groundwater, manufacturing, mining and chemical processing fluids and effluent, foodstuffs, and biological fluids of either animals or humans. Such biological fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

The calcium complexing compounds of this invention have the general structure

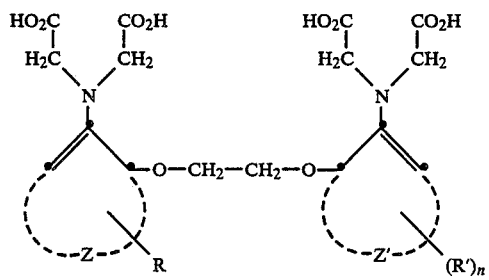

wherein Z and Z' independently represent the carbon and hetero atoms (oxygen, nitrogen, sulfur, selenium, tellerium) necessary to complete a 5- to 10-membered substituted or unsubstituted aromatic, unsaturated carbocyclic or unsaturated heterocyclic ring (single or fused ring), for example, benzene, naphthalene, terphenyl, thiazole, furan, thiophene, cycloheptatriene, oxazole, tellurazole and pyridine rings. These rings can be substituted with one or more alkyl group having 1 to 30 carbon atoms (for example, methyl, ethyl, dodecyl, pentacosanyl, and others known in the art), or other substituents readily ascertained by one skilled in the art. Preferably, Z and Z' independently represent the carbon atoms necessary to complete a substituted or unsubstituted 6-membered aromatic ring, for example, benzene, naphthalene and pyridine. Most preferably, each ring is a phenyl ring having up to 3 substituents such as alkyl as defined below, halo or alkoxy preferably of 1 to 20 carbon atoms.

In the illustrated structure, each R' is independently formyl, substituted or unsubstituted alkyl (preferably of 1 to 20 carbon atoms, for example, methyl, chloromethyl, ethyl, n-propyl, t-butyl, hexyl or dodecyl), substituted or unsubstituted acyl (that is, —COR" wherein R" is substituted or unsubstituted alkyl as defined above for R'), substituted or unsubstituted cycloalkyl preferably of 5 to 7 carbon atoms (for example, cyclopentyl or cyclohexyl) or halo (for example, fluoro, chloro or bromo). Preferably, R' is formyl or substituted or unsubstituted alkyl as defined above.

R is a dye moiety which is directly conjugated through the aromatic, unsaturated carbocyclic or unsaturated heterocyclic ring formed by Z to the nitrogen atom attached to the ring. Therefore, the dye moiety can be attached to any position of the ring which provides direct conjugation through the ring to the nitrogen atom. When the ring is a benzene ring, it is preferred that the dye moiety be in a position para to the nitrogen atom.

In the structure shown above, n is 0, 1 or 2. Preferably, n is 1.

As used in this specification and in the claims, the term "dye moiety" refers to either a moiety which is a chromogen itself, or a moiety which when attached to the Z ring illustrated above in a conjugated manner provides a chromogen. The chromogen has a maximum absorption greater than about 400 nm in the electromagnetic spectrum as opposed to one having maximum absorption in the ultraviolet region (generally less than 400 nm). Useful dye moieties include azo, pyrylium, triphenylmethane, cyanine and indoaniline. An azo moiety includes a substituted or unsubstituted aryl attached to the Z ring through a —N=N— linkage. A pyrylium dye moiety is a 6-membered unsaturated heterocycle having a calcogen atom, such as an oxygen or sulfur atom, in the ring. A triphenylmethane moiety is a benzene ring having two substituted or unsubstituted phenyl groups attached to it through a

linkage. The cyanine moiety includes any merocyanine, quinoline, benzoxazole or other heterocycle linked to the Z ring through a conjugated carbon chain. The azo and cyanine dye moieties are preferred in the practice of this invention.

Representative compounds of this invention are listed in Table I below with reference to the structure illustrated below immediately before Table I. Compounds 8, 17 and 20 are preferred in the practice of this invention.

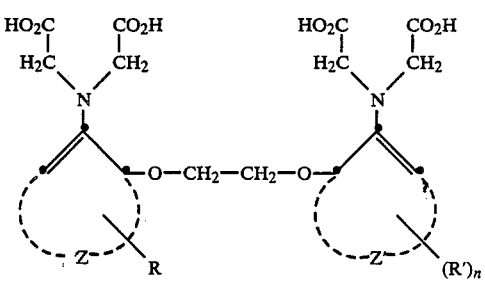

TABLE I

| Compound | Z | Z' | R | R' | n |
|---|---|---|---|---|---|
| 1 | dimethylphenyl (o or p) | same as Z | −N=N−(4-nitrophenyl) | — | 0 |
| 2 | " | " | " | −CH$_3$ | 1 |
| 3 | " | " | −N=N−(2-SO$_2$CH$_3$, 4-NO$_2$-phenyl) | −CH$_3$ | 1 |
| 4 | " | " | " | −Br | 1 |
| 5 | " | " | " | −CHO | 1 |
| 6 | " | dimethylphenyl | " | −t-butyl | 1 |
| 7 | " | " | " | −C$_{12}$H$_{25}$ | 1 |
| 8 | " | " | −N=N−(2-SO$_2$C$_6$H$_{13}$, 4-NO$_2$-phenyl) | " | 1 |
| 9 | " | dimethylphenyl | −CH=CH−(4-(2,6-di-t-butyl-thiopyrylium)) ClO$_4^-$ | — | 0 |
| 10 | " | " | Same as for Compound 9 except sulfur atom is replaced with selenium atom. | " | 0 |
| 11 | " | " | Same as for Compound 9 except sulfur atom is replaced with tellurium atom, and anion is BF$_4^-$. | " | 0 |
| 12 | " | " | −CH=CH−(4-(2,6-diphenyl-thiopyrylium)) PF$_6^-$ | " | 0 |

TABLE I-continued

| Compound | Z | Z' | R | R' | n |
|---|---|---|---|---|---|
| 13 | " | " | Same as for Compound 12 except sulfur atom is replaced with selenium atom, and anion is $ClO_4^-$. | " | 0 |
| 14 | " | " | Same as for Compound 12 except sulfur atom is replaced with tellurium atom. | " | 0 |
| 15 | " | (phenyl) | (triaminotriphenylmethane cation with $(CH_3)_3N^+$ and $N(CH_3)_2$ groups, $Cl^-$) | $-CH_3$ | 1 |
| 16 | (naphthyl) | (phenyl) | Same as for Compound 8. | $-C_{12}H_{25}$ | 1 |
| 17 | (phenyl) | Same as for Compound 9. | $-CH=CH-$ (naphthyl with $N^+$-ethyl, $ClO_4^-$) | — | 0 |
| 18 | " | (phenyl) | $-N=N-$ C(CH$_3$)= with N, S, $NO_2$ substituted thiazole | $-CH_3$ | 2 |
| 19 | (naphthyl) | (phenyl) | " | tert-butyl | 1 |
| 20 | (phenyl) | (phenyl) | $-N=N-$ C(CH$_3$)= with N, S fused benzothiazole bearing $NO_2$ | tert-butyl | 1 |

TABLE I-continued

| Compound | Z | Z' | R | R' | n |
|---|---|---|---|---|---|
| 21 | " | " | 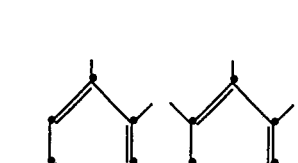 | " | 1 |
| 22 | 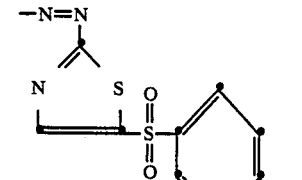 | | 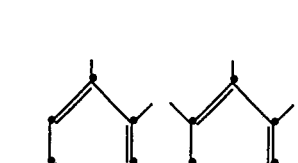 | —CH₃ | 2 |

The compounds of this invention can be prepared according to several general procedures each specific to the type of dye moiety used. Representative synthetic methods are illustrated in the Examples 1–3 below. All of the starting materials are readily available to a skilled chemist.

The calcium complexing compounds of this invention are generally soluble in water. They can be used in aqueous compositions buffered to a pH of from about 6 to about 9 with one or more suitable buffers, for example, phosphate, borate, citrate, 2-(4-morpholino)ethanesulfonic acid (MES), 2-[tris(hydroxymethyl)methylamino]-1-ethanesulfonic acid (TES), tris(hydroxymethyl)aminomethane (TRIS), and others known in the art. Other useful buffers are reported by Good et al in *Biochem.*, 5, 467 (1966), and *Anal. Biochem.*, 104, 300 (1980).

Generally, an aqueous composition of the present invention comprises at least about 50, and preferably from about 100 to about 300, μmolar calcium complexing compound of this invention. The concentration of the buffer is within the skill of a worker in the art.

A solution assay for calcium ions is generally carried out by mixing the compound of the invention with a sample of fluid suspected of containing calcium ions in a suitable container (for example, test tube, petri dish, beaker or cuvette). Solutions with high calcium ion concentrations may be diluted prior to addition of the compound of the invention. The resulting solution is mixed for a relatively short time (for example, about 2 minutes) at any suitable temperature (generally at about 25° C.). The solution is then evaluated by measuring the optical density change (that is, the shift in spectral absorption) caused by the complexation of the compound with calcium ions at the appropriate wavelength using suitable colorimetric detection equipment. The shift in absorption can be a change from one wavelength in the visible region to another wavelength in the visible region. However, many compounds of this invention become colorless when they complex with calcium ions. Hence, in such cases, the shift in absorption is a disappearance of color. Generally, the compounds of this invention absorb at a wavelength greater than about 400 nm before complexation, and absorb at a wavelength less than 400 nm when complexed with calcium ions. Preferably, the compounds absorb at a wavelength greater than about 600 nm prior to complexation.

The assay can also be carried out by contacting a porous absorbent material, for example, a paper strip, containing the sample of fluid to be tested, with the composition of this invention. The calcium ions in the absorbent material can migrate into the composition and promote the optical density change needed for ion determination.

The method of this invention can also be practiced with a dry analytical element. The simplest element can be composed of an absorbent carrier material, for example, a thin sheet of a self-supporting absorbent or bibulous material, such as filter paper or strips, which contain the complexing compound of this invention. The element can be divided into two or more discrete zones with different reagents incorporated into individual zones of the carrier material. Such elements are know in the art as test strips, diagnostic elements, dip sticks, diagnostic agents and the like.

When employed in dry analytical elements, the compound of this invention can be incorporated into a suitable absorbent carrier material by imbibition or impregnation, or can be coated on a suitable material. Alternatively, it can be added to the element during an assay. Useful absorbent carrier materials are insoluble and maintain their structural integrity when exposed to water or biological fluids such as whole blood or serum. Useful elements can be prepared from paper, porous particulate structures, porous polymeric films, cellulose, glass fiber, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and 4,312,834 (issued Jan. 26, 1982 to Vogel et al).

Preferably, the dry analytical element of this invention comprises a porous spreading zone which acts as an absorbent carrier material. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (transmission or reflectance spectroscopy). Useful supports can be prepared from paper, metal foils, polystyrene, polyesters, polycarbonates, cellulose esters and others known in the art.

The porous spreading zone can be prepared from any suitable fibrous or non-fibrous material or mixtures of either or both. The void volume and average pore size of this zone can be varied depending upon the use intended. Useful spreading zones can be prepared using fibrous or nonfibrous materials, either mixed with a suitable binder material or woven into a fabric, as described in U.S. Pat. Nos. 4,292,272 (issued Sept. 29, 1981 to Kitajima et al), 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57 (1982)-101760 (published June 24, 1982). It is desirable that the spreading zone be isotropically porous, meaning that the porosity is the same in each direction in the zone as caused by interconnected spaces or pores between particles, fibers or polymeric strands.

The elements can have two or more discrete zones, either in the same layer or superimposed. At least one of these zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, all reagents become mixed and can readily move within the element as a composition. Preferably, the zones in the element are separately coated superposed layers, although two or more zones can be separate areas in a single layer of the element.

In the elements, the complexing compound of this invention is generally present in one or more zones in a coverage of at least about 0.25, and preferably from about 0.25 to about 1.5, $g/m^2$. Other reagents and materials are present in coverages within the skill of a worker in the art.

The elements of this invention can also contain one or more other addenda commonly put in the elements for various manufacturing or operational advantages. Such addenda include surfactants, buffers, solvents, hardeners and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, calcium ion determination is made by taking the element from a supply roll, chip packet or other source and physically contacting it with a sample (for example, up to 1 to 200 μl) of the fluid to be tested so that the sample and reagents within the element become mixed. Such contact can be accomplished in any suitable manner, for example, by dipping or immersing the element into the sample or, preferably, by spotting the element by hand or machine with a drop of the sample with a suitable dispensing means.

After sample application, the element can be exposed to conditioning, such as incubation, heating or the like, that may be desirable to quicken or otherwise facilitate obtaining any test result. The shift in absorbance is then measured to determine the amount of calcium ions in the test fluid.

In the following examples which illustrate the practice of this invention, the materials used were obtained either from Eastman Kodak Company (Rochester, N.Y.) or other commercial sources, or prepared using standard procedures and readily available starting materials.

EXAMPLE 1

Preparation of Complexing Compound 6

The compound of this invention identified as Complexing Compound 6 on Table I above was prepared in the following manner.

STEP A: Preparation of 1-(2-nitro-4-tert-butylphenoxy)-2-(2-nitrophenoxy)ethane:

2-Nitrophenol (60.3 g, 0.434 mole) was heated with potassium hydroxide (24.3 g, 0.434 mole) in 200 ml of N,N-dimethylformamide at 50° C. until the solution became homogeneous. 2-Bromoethanol (64.6 g, 0.521 mole) was added and the resulting solution was heated to 120° C. for 40 minutes. The solution was cooled and aqueous potassium carbonate and ethyl ether were added. Three phases formed of which the bottom phase contained no product and was discarded. The top ether phase contained product and was separated. The middle phase was extracted with dichloromethane. The combined organic phases were washed five times with water to remove N,N-dimethylformamide, then dried over disodium sulfate and evaporated to give 57.0 g of the compound

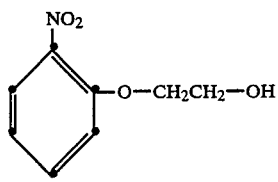

as an oil (72%). Tosylation of this compound (50.0 g, 0.275 mole) was effected by treatment with p-toluenesulfonyl chloride (59.2 g, 0.31 mole) at −20° C. in pyridine for twenty hours. The resulting solution was poured into cold dilute HCl, and the precipitate formed was recrystallized from ethanol to give 72 g (77% yield) of the compound

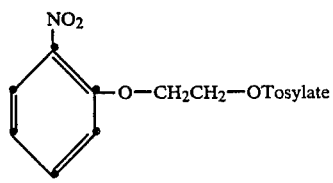

A mixture of 2-nitro-4-t-butylphenol (5.48 g, 28.1 mmole) and potassium hydroxide (1.57 g, 2.8 mmole)

was heated in 50 ml of N,N-dimethylformamide until dissolved. The tosylated compound illustrated above (9.50 g, 28.2 mmole) was added and the mixture was heated at 120° C. for two hours. The resulting solution was cooled and partitioned between dichloromethane and water. The organic phase was extracted twice with water and once with brine, dried over disodium sulfate, filtered and evaporated to leave a yellow oil which was purified by chromatography on silicon dioxide with 1:1 by volume dichloromethane: ligroine to yield the desired crystalline product (6.7 g, 66%), m.p. 114.5°–116.5° C.

Calculated elemental analysis for $C_{18}H_{20}N_2O_6$: C, 60.0, H, 5.6, N, 7.8. Found: C, 59.8, H, 5.6, N, 7.7.

See Angelici et al, *Inorg. Chem.*, 21, pp. 2178–2184 (1982).

STEP B: Preparation of 1-(2-amino-4-t-butylphenoxy)-2-(2-aminophenoxy)ethane:

The compound prepared in Step A (6.1 g, 17 mmole) was suspended in 100 ml of absolute ethanol with 0.20 g of 10% Pd/C and the mixture was heated to reflux. Hydrazine (5 ml) was added and the resulting solution was refluxed for 30 minutes. The solution was filtered while hot through celite, then cooled to 0° C. The resulting white precipitate was collected and dried to give 4.7 g of the desired product (92%), m.p. 147.5°–150.5° C.

Calculated elemental analysis for $C_{18}H_{24}N_2O_2$: C, 72.0, H, 8.1, N, 9.3. Found: C, 72.4, H, 8.2, N, 9.4.

STEP C: Preparation of

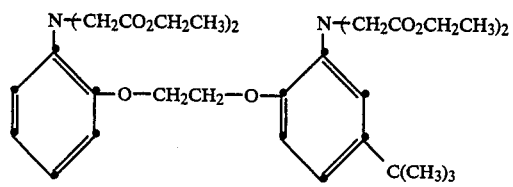

This compound was prepared by refluxing the compound from Step B (3.00 g, 10.0 mmole) in 100 ml of acetonitrile together with 16.8 g of ethyl bromoacetate (100 mmole) and lutidine (10.8 g, 100 mmole) for two days. The solution was then filtered and the filtrate was partitioned between dichloromethane and water. The organic phase was separated and extracted twice with dilute HCl and once with brine. The organic phase was dried over disodium sulfate, filtered and evaporated to leave an oil which was purified by chromatography on silicon dioxide with a gradient from dichloromethane to 5% ethyl acetate/dichloromethane. The product thus obtained was recrystallized from ethanol to give the desired compound (4.5 g, 70%), m.p. 89.5°–91.5° C.

Calculated elemental analysis for $C_{34}H_{48}N_2O_{10}$: C, 63.3, H, 7.5, N, 4.3. Found: C, 63.1, H, 7.3, N, 3.9.

STEP D:

The product of Step C (3.2 g, 5.0 mmole) was suspended in 75 ml of methanol and 1.2 g of sodium hydroxide (30 mmole) was added in 7.5 ml of water. The solution was heated at 50° C. for 30 minutes, cooled and concentrated in vacuo. The residue was dissolved in water which was then acidified with concentrated HCl. The precipitate was collected, washed with water and dried to give 1.7 g of the desired compound (64%):

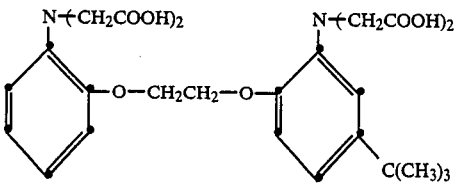

STEP E:

The product of Step D (1.6 g, 3.01 mmole) was dissolved in methanol (300 ml) and cooled in a dry ice-acetone bath. A diazonium salt, 2-mesyl-4-nitrobenzenediazonium hexafluorophosphate (1.12 g, 3 mmole), was dissolved in 300 ml of acetone and added dropwise to the solution of the tetraacid over a 30 minute period. The reaction mixture was then warmed to room temperature and concentrated in vacuo. the residue was dissolved in methanol (20 ml) and poured into water (200 ml). The precipitate was collected by filtration, washed with water and dried to yield a dark-colored solid. A solution of the compound in borate buffer (pH 9.3) was violet in color with a $\lambda_{max}$ of 570 nm and $\epsilon = 27,200 M^{-1} cm^{-1}$ (2 g, 86%).

Analytical data: $^1$H-NMR [$(CD_3)_2CO$] 1.07 (s, 9H, $C(CH_3)_3$), 3.08 (s, 4H, $SO_2CH_3$), 3.62 (s, 4H, $NCH_2$), 3.88 (bs, 8H, $NCH_2$, $OCH_2$), 6.20–6.75 (m, 7H, ArH, $CO_2H$), 7.07–7.50, 8.00–8.40 (m, 6H, ArH).

Calculated elemental analysis for $C_{33}H_{37}N_5O_{14}S$: C, 52.2, H, 4.9, N, 9.2, S, 4.2. Found: C, 51.8, H, 4.4, N, 9.4, S, 4.5.

EXAMPLE 2

Preparation of Complexing Compound 10

The compound identified herein as Complexing Compound 10 of Table I above was prepared in the following manner.

STEP A:

A compound (20.0 g, 34.0 mmole) of the following structure

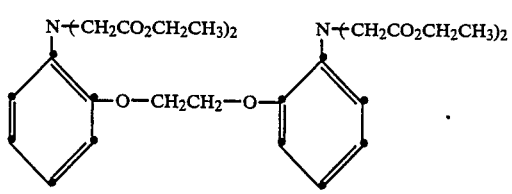

was dissolved in 100 ml of N,N-dimethylformamide. $POCL_3$ (10.1 g, 66 mmole) was added and the mixture was heated for four hours at 100° C., then poured into a solution of sodium acetate. After 16 hours of standing, the precipitate was collected and purified by chromatography on silicon dioxide with 20% ethyl acetate/toluene to give the desired product (6.3 g, 30%) of the structure

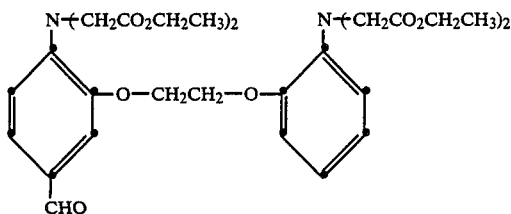

without contamination from unreacted starting material or dialdehyde.

Calculated elemental analysis for $C_{31}H_{40}N_2O_{11}$: C, 60.4, H, 6.5, N, 4.5. Found: C, 60.6, H, 6.6, N, 4.4.

STEP B:

The tetraester aldehyde (3.08 g, 5.00 mmole) prepared in Step A was added to 75 ml of methanol and stirred while 1.2 g of sodium hydroxide (30 mmole) in 7.5 ml of water was added. The resulting solution was heated at 50° C. for 30 minutes then concentrated in vacuo. The residue was dissolved in water then acidified with HCl. The resulting tacky precipitate was collected, chilled in cold water, ground to a fine powder and filtered to yield, after drying, 2.0 g (79%) of the compound

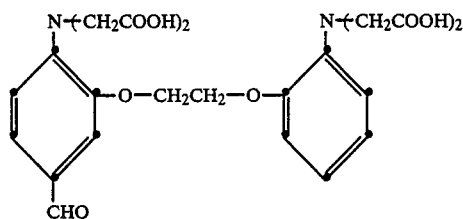

Calculated elemental analysis for $C_{23}H_{24}N_2O_{11}$: c, 54.8, H, 4.8, N, 5.6. Found: C, 54.5, H, 5.0, N, 5.1

See Tsien, *Biochem.*, 19, pp. 2396–2404 (1980).

STEP C:

The compound prepared in Step B (1.01 g, 2.00 mmole) and a pyrylium salt (0.74 g, 2.0 mmole) of the structure

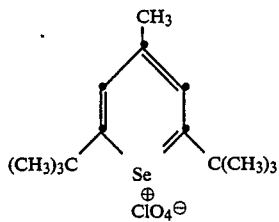

prepared by the technique described for the tellurium analog by Detty et al, *Organometallics*, 5, pp. 2250–2256 (1986) were heated in 100 ml of n-propanol for 30 minutes at 100° C. The resulting deep blue solution was concentrated in vacuo, and then triturated with ethyl ether. Filtration and drying yielded a deep maroon-colored solid (1.5 g, 88%) which was the desired complexing compound.

Calculated elemental analysis for $C_{37}H_{45}ClN_2O_{14}Se \cdot H_2O$ was: C, 50.8, H, 5.4, N, 3.2; Found: C, 50.7, H, 5.3, N, 2.9.

A small amount of this complexing compound was dissolved in dilute aqueous sodium bicarbonate to give a dark blue colored solution ($\lambda_{max} = 620$ nm). When calcium chloride was added, the solution became colorless whereas, no change in color was observed when magnesium chloride was added.

EXAMPLE 3

Preparation of Complexing Compound 17

The compound identified in Table I above as Complexing Compound 17 was prepared in the following manner.

STEP A: Preparation of N-ethylbenz[cd]indol-2(1H)-one:

A mixture of benz[cd]indol-2(1H)-one (15.0 g, 88.8 mmole) in 20% aqueous potassium hydroxide (200 ml) was heated at 55°–60° C. while 60 ml of diethyl sulfate was added dropwise over a three hour period. After 16 hours at room temperaure and an additional hour at 55°–60° C., the mixture was partitioned between dichloromethane and water. The organic phase was concentrated and purified by chromatography on silicon dioxide with 5% acetone/dichloromethane to give the desired product (8.0 g, 46%).

STEP B: Preparation of Perchlorate:

The compound prepared in Step A (1.97 g, 10.0 mmole) was dissolved under nitrogen in 5 ml of dry tetrahydrofuran. A solution of 5 ml of 3 molar $CH_3MgBr$ in ethyl ether (15 mmole) was added at 0° C. After one hour, 10 ml of 3 molar $CH_3MgBr$ was added and the solution was refluxed for 10 minutes. The mixture was then poured into 200 g of ice to which 20 ml of 70% $HClO_4$ had been added. The resulting precipitate was removed by filtration and washed well with water, then dried to give 2.43 g of product (82%), m.p. 215°–218° C. (decomposed), having the structure:

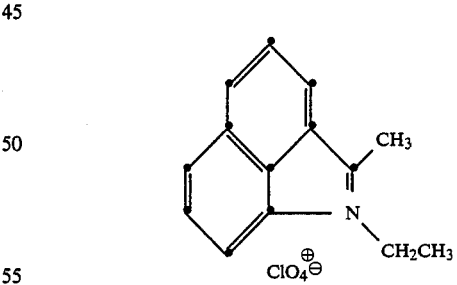

Calculated elemental analysis for $C_{14}H_{14}ClNO_4$ was: C, 56.9, H, 4.8, N, 4.7. Found: C, 56.5, H, 4.6, N, 4.4.

STEP C:

By the procedure described in Example 2, the compound prepared in Step B of that Example (0.25 g, 0.50 mmole) and the compound prepared in Step B of this example (0.15 g, 0.51 mmole) were allowed to react in ethanol, forming a styryl dye (0.34 g, 87%) of the structure:

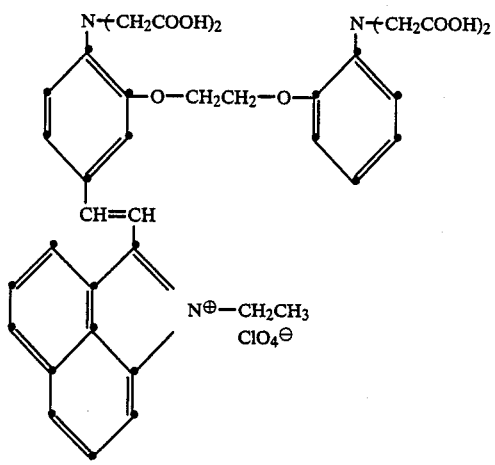

In phosphate buffer at pH 7.0, the dye in the absence of calcium ion had a $\lambda_{max}=640$ nm, $\epsilon=34,600 M^{-1}cm^{-1}$. Upon addition of calcium ion, the $\lambda_{max}$ was 500 nm, $\epsilon=18,800 M^{-1}cm^{-1}$. The extinction coefficient of the dye-calcium complex at 640 nm decreased to $9,100 M^{-1}cm^{-1}$.

Calculated elemental analysis for $C_{37}H_{36}ClN_3O_{14}$ was: C, 56.8, H, 4.6, N, 5.4. Found: C, 56.9, H, 4.6, N, 5.3.

EXAMPLE 4

Solution Assay for Calcium Ions Using Complexing Compound 1

A solution assay for calcium ions was carried out by adding Complexing Compound 1 to borate buffer (pH 8.5) containing various amounts of calcium and magnesium ions, and measuring any resulting change in absorbance (A). The concentration of Complexing Compound 1 was maintained at $5.0\times10^{-3}$ molar. The results are presented in Table II below.

TABLE II

| Calcium Ion Concentration Millimolar | Magnesium Ion Concentration Millimolar | A (500 nm) | A (390 nm) |
|---|---|---|---|
| 0 | 0 | 11.40 | 2.90 |
| 0.50 | 0 | 10.75 | 3.25 |
| 1.00 | 0 | 9.45 | 3.88 |
| 1.50 | 0 | 8.35 | 4.55 |
| 2.00 | 0 | 7.40 | 5.30 |
| 2.50 | 0 | 6.15 | 5.95 |
| 3.00 | 0 | 5.10 | 6.75 |
| 3.50 | 0 | 3.82 | 7.45 |
| 4.00 | 0 | 2.85 | 8.05 |
| 4.50 | 0 | 2.35 | 8.35 |
| 5.00 | 0 | 2.18 | 8.35 |
| 7.50 | 0 | 1.98 | 8.60 |
| 10.00 | 0 | 1.80 | 8.35 |
| 0 | 0 | 11.20 | — |
| 0 | 5.00 | 10.80 | — |
| 0 | 10.00 | 10.80 | — |
| 0 | 50.00 | 9.60 | — |

It can be seen from the data in Table II that the presence of calcium ions is detected by a shift in absorbance from 500 nm to 390 nm which is indicative of the formation of magnesium ions did not cause an absorbance shift until very high concentrations were present ($50\times10^{-3}$ molar).

EXAMPLE 5

Solution Assay for Calcium Ions Using Complexing Compound 17

A solution assay was carried out like that of Example 4 using Compound 17 ($5.06\times10^{-5}$ molar) in phosphate buffer (pH 7.0). The results are shown in Table III.

A large change in magnesium ion concentration (0 to $50\times10^{-5}$ molar) caused very little shift in the absorbance (1.75 to 1.68). This indicates that the Complexing Compound does not complex with magnesium ions to a significant degree. The absorbance of the compound with magnesium ions at 500 nm was not measured because the absorbance change was too small to be significant. The calcium ion concentration, however, caused a significant change in absorbance at all concentrations.

TABLE III

| Calcium Ion Concentration Millimolar | Magnesium Ion Concentration Millimolar | A (640 nm) | A (500 nm) |
|---|---|---|---|
| 0 | 0 | 1.75 | 0.18 |
| $0.50\times10^{-2}$ | 0 | 1.63 | 0.21 |
| $1.00\times10^{-2}$ | 0 | 1.58 | 0.25 |
| $1.50\times10^{-2}$ | 0 | 1.46 | 0.28 |
| $2.00\times10^{-2}$ | 0 | 1.44 | 0.31 |
| $2.50\times10^{-2}$ | 0 | 1.36 | 0.36 |
| $5.00\times10^{-2}$ | 0 | 1.12 | 0.48 |
| $5.50\times10^{-2}$ | 0 | 1.12 | 0.52 |
| $6.00\times10^{-2}$ | 0 | 1.08 | 0.60 |
| $10.00\times10^{-2}$ | 0 | 0.87 | 0.65 |
| $20.00\times10^{-2}$ | 0 | 0.66 | 0.79 |
| $50.00\times10^{-2}$ | 0 | 0.46 | 0.95 |
| 0 | $50.0\times10^{-2}$ | 1.68 | — |

EXAMPLE 6

Dry Assay for Calcium Ions

An analytical element of the present invention was prepared having the following format:

| | | |
|---|---|---|
| Spreading Layer | Poly(vinyltoluene-co-p-t-butylstyrene-co-metacrylic acid) beads | 25–300 g/m² |
| | Poly(N—isopropylacrylamide) adhesive | 0.1–1 g/m² |
| | Sodium dodecyl sulfate | 0.1–5 g/m² |
| Subbing Layer | Poly(vinyl pyrrolidone) | 0.5–2 g/m² |
| Reagent/ Registration Layer | Gelatin (hardened) | 2–20 g/m² |
| | Trishydroxymethyl methylaminopropane sulfonic acid buffer (pH 8) | 0.1–10 g/m² |
| | Sodium dodecyl sulfate | 0.1–5 g/m² |
| | Calcium Compound 6 (from Table I) | 0.1–1.5 g/m² |
| | Poly(ethylene terephthalate) Support | |

This element was used to determine calcium ions in bovine serum albumin in the following manner. Samples (10 μl) of the protein containing various concentrations of calcium ions (2–20 mg/dl) were applied to the element. The reflection density resulting from complexation of the calcium ions with the calcium complexing compound in the element was measured after 5 minutes at 630 nm using a commerically available spectrophotometer. A plot of each reflection density measured at 5 minutes vs. concentration of calcium ions was linear.

The invention has been described in detail with particular reference to preferred embodiments thereof, but it will be understood that variations and modifications can be effected within the spirit and scope of the invention.

We claim:

1. A substituted or unsubstituted compound of the structure

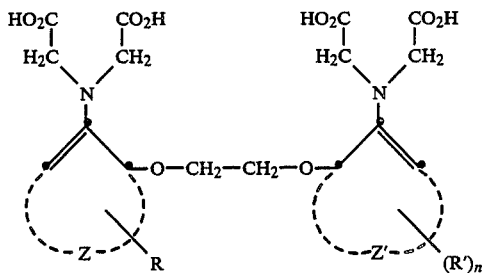

wherein Z and Z' independently represent the carbon, oxygen, nitrogen, sulfur, selenium and tellerium atoms necessary to complete a 5- to 10-membered aromatic, unsaturated carbocyclic or unsaturated heterocyclic ring, R is a dye moiety which is directly conjugated through said ring to the nitrogen atom, each R' is independently formyl, substituted or unsubstituted alkyl, substituted or unsubstituted acyl or halo and n is 0, 1 or 2, provided that said compound exhibits a maximum electromagnetic absorption greater than about 400 nm in the absence of calcium ions.

2. The compound of claim 1 wherein Z and Z' independently represent the carbon atoms necessary to complete a 6-membered aromatic ring.

3. The compound of claim 1 wherein said dye moiety is an azo, pyrylium, triphenylmethane or cyanine dye moiety.

4. The compound of claim 3 wherein said dye moiety is an azo or cyanine dye moiety.

5. An aqueous composition buffered to a pH of from about 6 to about 9 and containing a substituted or unsubstituted compound of the structure

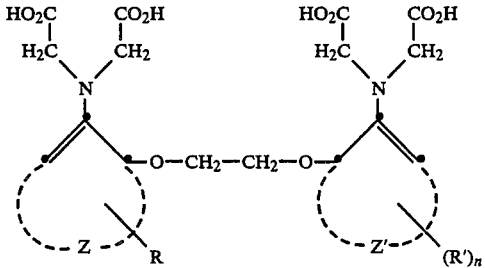

wherein Z and Z' independently represent the carbon, oxygen, nitrogen, sulfur, selenium and tellerium atoms necessary to complete a 5- to 10-membered aromatic, unsaturated carbocyclic or unsaturated heterocyclic ring, R is a dye moiety which is directly conjugated through said ring to the nitrogen atom, each R' is independently formyl, substituted or unsubstituted alkyl, substituted or unsubstituted acyl or halo and n is 0, 1 or 2, provided that said compound exhibits a maximum electromagnetic absorption greater than about 400 nm in the absence of calcium ions.

6. The composition of claim 5 wherein said dye moiety is an azo, pyrylium, triphenylmethane or cyanine dye moiety.

7. The composition of claim 5 wherein Z and Z' independently represent the carbon atoms necessary to complete a 6-membered aromatic ring.

8. An analytical element for the determination of calcium ions comprising an absorbent carrier material containing a substituted or unsubstituted compound of the structure

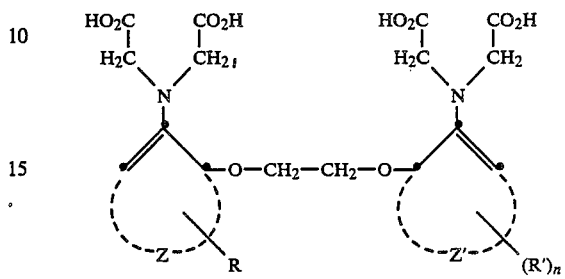

wherein Z and Z' independently represent the carbon, oxygen, nitrogen, sulfur, selenium and tellerium atoms necessary to complete a 5- to 10-membered aromatic, unsaturated carbocyclic or unsaturated heterocyclic ring, R is a dye moiety which is directly conjugated through said ring to the nitrogen atom, each R' is independently formyl, substituted or unsubstituted alkyl, substituted or unsubstituted acyl or halo and n is 0, 1 or 2, provided that said compound exhibits a maximum electromagnetic absorption greater than about 400 nm in the absence of calcium ions.

9. An analytical element for the determination of calcium ions comprising a nonporous support having thereon a reagent zone and a porous spreading zone, said element containing in at least one of said zones a substituted or unsubstituted compound of the structure

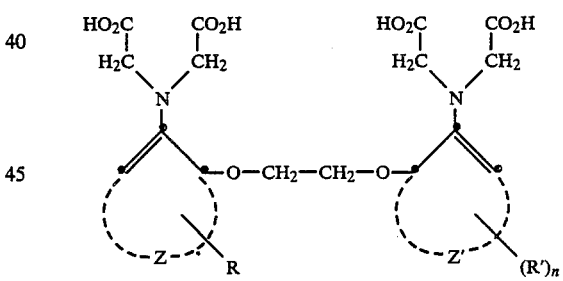

wherein Z and Z' independently represent the carbon, oxygen, nitrogen, sulfur, selenium and tellurium atoms necessary to complete a 5- to 10-membered aromatic, unsaturated carbocyclic or unsatured heterocyclic ring, R is a dye moiety which is directly conjugated through said ring to the nitrogen atom, each R' is independently formyl, substituted or unsubstituted alkyl, substituted or unsubstituted acyl or halo and n is 0, 1 or 2, provided that said compound exhibits a maximum electromagnetic absorption greater than about 400 nm in the absence of calcium ions.

10. The element of claim 9 wherein said zones are superposed layers.

11. The element of claim 9 wherein said calcium complexing compound is in said reagent zone.

12. The element of claim 9 wherein said dye moiety is an azo, pyrylium, triphenylmethane or cyanine dye moiety.

13. The element of claim 9 wherein Z and Z' represent the carbon atoms necessary to complete a benzene ring and said dye moiety is in a position para to the nitrogen atom.

14. A method for the determination of calcium ions comprising the steps of:

A. contacting a sample of a liquid suspected of containing calcium ions with a substituted or unsubstituted compound of the structure

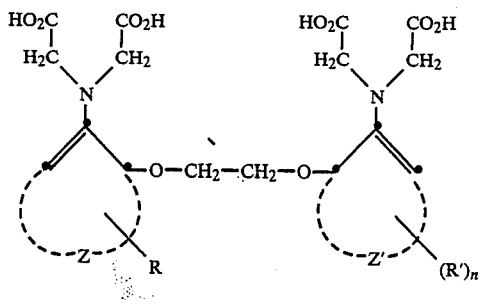

wherein Z and Z' independently represent the carbon, oxygen, nitrogen, sulfur, selenium and tellerium atoms necessary to complete a 5- to 10-membered aromatic, unsaturated carbocyclic or unsaturated heterocyclic ring, R is a dye moiety which is directly conjugated through said ring to the nitrogen atom, each R' is independently formyl, substituted or unsubstituted alkyl, substituted or unsubstituted acyl or halo and n is 0, 1 or 2, provided that said compound exhibits a maximum electromagnetic absorption greater than about 400 nm in the absence of calcium ions, and B. determining the optical density change resulting from the complexation of calcium ions with said compound.

15. The method of claim 14 wherein said liquid is a biological fluid.

16. The method of claim 14 wherein said optical density change results from a shift in absorbance maximum to a shorter wavelength.

* * * * *